US00RE51132E

(19) United States
(12) Reissued Patent
Rao et al.

(10) Patent Number: US RE51,132 E
(45) **Date of Reissued Patent: *Nov. 24, 2026**

(54) PROCESSES FOR THE PRODUCTION OF FLUOROPROPANES AND HALOPROPENES

(71) Applicant: THE CHEMOURS COMPANY FC, LLC, Wilmington, DE (US)

(72) Inventors: Velliyur Nott Mallikarjuna Rao, Wilmington, DE (US); Allen Capron Sievert, Elkton, MD (US)

(73) Assignee: THE CHEMOURS COMPANY FC, LLC, Wilmington, DE (US)

( * ) Notice: This patent is subject to a terminal disclaimer.

(21) Appl. No.: 18/412,856

(22) Filed: Jan. 15, 2024

Related U.S. Patent Documents

Reissue of:
(64) Patent No.: 8,318,992
Issued: Nov. 27, 2012
Appl. No.: 12/444,462
PCT Filed: Oct. 31, 2007
PCT No.: PCT/US2007/022995
§ 371 (c)(1),
(2) Date: Jan. 7, 2010
PCT Pub. No.: WO2008/054782
PCT Pub. Date: May 8, 2008

U.S. Applications:
(63) Continuation of application No. 14/552,613, filed on Nov. 25, 2014, now Pat. No. Re. 49,849, which is an application for the reissue of Pat. No. 8,318,992.

(60) Provisional application No. 60/855,538, filed on Oct. 31, 2006.

(51) Int. Cl.

| | |
|---|---|
| ***C07C 17/21*** | (2006.01) |
| ***B01J 23/26*** | (2006.01) |
| ***C07C 17/06*** | (2006.01) |
| ***C07C 17/10*** | (2006.01) |
| ***C07C 17/20*** | (2006.01) |
| ***C07C 17/25*** | (2006.01) |
| ***C07C 19/08*** | (2006.01) |
| ***C07C 21/18*** | (2006.01) |

(52) U.S. Cl.
CPC ..... *C07C 17/21* (2013.01); *B01J 23/26* (2013.01); *C07C 17/06* (2013.01); *C07C 17/10* (2013.01); .. *C07C 17/206* (2013.01); *C07C 17/25* (2013.01); *C07C 19/08* (2013.01); *C07C 21/18* (2013.01)

(58) Field of Classification Search
CPC ..... C07C 17/21; C07C 17/06; C07C 17/10; C07C 17/206; C07C 17/25; C07C 19/08; C07C 21/18; B01J 23/26
See application file for complete search history.

(56) References Cited

U.S. PATENT DOCUMENTS 2,787,646 A 4/1957 Haszeldine
2,808,425 A 10/1957 Haszeldine
(Continued)

FOREIGN PATENT DOCUMENTS

JP 4966613 A 6/1974
JP 49066613 6/1974
(Continued)

OTHER PUBLICATIONS

File History for U.S. Appl. No. 60/855,540, (2006).
Haszeldine, R.N., Reactions of fluorocarbon radicals. Part V. Alternative syntheses for trifluoromethylacetylene (3:3:3-trifluoropropyne), and the influence of polyfluoro-groups on adjacent hydrogen and halogen atoms, Journal of Chemical Society, 1951, pp. 2495-2504.
Satterfield, Charles N., Heterogeneous Catalysis in Industrial Practice, Catalyst Preparation and Manufacture, Chapter 4, 1991, pp. 87-112, McGraw-Hill, New York.
Büchner M. et al., Reactions of Gaseous, Halogenated Propene Radical Cations with Ammonia: A Study of the Mechanism by Fourier Transform Ion Cyclotron Resonance; Chemistry: A European Journal, 1998, pp. 1799-1809, vol. 4.
Curriculum Vitae of Dr. Joseph Thrasher.
Declaration of Dr. Joseph Thrasher.
(Continued)

*Primary Examiner* — Alan D Diamond

(57) ABSTRACT

A process is disclosed for making $CF_3CF_2CH_3$, $CF_3CF{=}CH_2$, [and/or] $CF_3CCl{=}CH_2$, *$CF_3CCl{=}CH$ (1233xf), and/or $CH_3CH{=}CHCl$ (1233zd)*. The process involves reacting at least one starting material selected from the group consisting of halopropanes of the formula $CX_3CH_2CH_2X$, halopropenes of the formula $CX_3CH{=}CH_2$ and halopropenes of the formula $CX_2{=}CHCH_2X$, wherein each X is independently F or Cl, with HF and $Cl_2$ in a reaction zone to produce a product mixture comprising [HCl, $CF_3CF_2CH_3$, $CF_3CF{=}CH_2$, and $CF_3CCl{=}CH_2$; and recovering the $CF_3CF_2CH_3$, $CF_3CF{=}CH_2$ and/or $CF_3CCl{=}CH_2$ from the product mixture.] *at least one of $CF_3CH_2CHF_2$(245fa), $CH_3CH{=}CH_2$ (1234yf) $CH_3CH{=}CHF$ (1234ze), $CF_3CCl{=}CH_2$ (1233xf) and $CF_3CH{=}CHCl$ (1233zd)*. [Also disclosed is a process for making $CF_3CH_2CHF_2$, $CF_3CH{=}CHF$, and/or $CF_3CH{=}CHCl$. This process involves reacting at least one starting material selected from the group consisting of halopropenes of the formula $CX_3CH{=}CH_2$ and halopropenes of the formula $CX_2{=}CHCH_2X$, wherein each X is independently F or Cl, with HF and $Cl_2$ in a reaction zone to produce a product mixture comprising HF, HCl, $CF_3CH_2CHF_2$, $CF_3CH{=}CHF$ and $CF_3CH{=}CHCl$; and recovering the $CF_3CH_2CHF_2$, $CF_3CH{=}CHF$, and/or $CF_3CH{=}CHCl$ from the product mixture.] The molar ratio of HF to the total amount of starting materials fed to the reaction zone [for both of these processes] is at least stoichiometric, and the molar ratio of $Cl_2$ to total amount of starting material fed to the reaction zone for [both of these processes] *the process* is 2:1 or less.

46 Claims, No Drawings

(56) References Cited

U.S. PATENT DOCUMENTS

| | | | | |
|---|---|---|---|---|
| 2,889,379 | A | 6/1959 | Ruh et al. | |
| 2,996,555 | A | 8/1961 | Rausch | |
| 3,632,834 | A | 1/1972 | Christoph | |
| 4,192,822 | A | 3/1980 | Sweeney et al. | |
| 4,605,802 | A | 8/1986 | Astrologes | |
| 4,650,914 | A | 3/1987 | Woodard | |
| 4,766,260 | A | 8/1988 | Manzer et al. | |
| 5,057,634 | A | 10/1991 | Webster et al. | |
| 5,177,273 | A | 1/1993 | Bruhnke et al. | |
| 5,264,639 | A | 11/1993 | Morikawa et al. | |
| 5,396,000 | A | 3/1995 | Nappa et al. | |
| 5,788,886 | A | 8/1998 | Minor et al. | |
| 5,895,825 | A | 4/1999 | Elsheikh et al. | |
| 5,986,151 | A | 11/1999 | Van Der Puy | |
| 6,013,846 | A | 1/2000 | Wismer et al. | |
| 6,111,150 | A | 8/2000 | Sakyu et al. | |
| 6,124,510 | A | 9/2000 | Elsheikh et al. | |
| 6,184,426 | B1 | 2/2001 | Belen'Kill et al. | |
| 6,224,781 | B1 | 5/2001 | Mahler et al. | |
| 6,291,730 | B1 | 9/2001 | Baker et al. | |
| 6,329,559 | B1 * | 12/2001 | Sievert et al. | 570/165 |
| 6,540,933 | B1 | 4/2003 | Sievert et al. | |
| 7,189,884 | B2 | 3/2007 | Mukhopadhyay et al. | |
| 8,318,992 | B2 | 11/2012 | Rao et al. | |
| 8,398,882 | B2 | 3/2013 | Rao et al. | |
| 8,450,537 | B2 * | 5/2013 | Rao | C07C 19/08 570/156 |
| 8,633,340 | B2 | 1/2014 | Smith et al. | |
| 10,214,669 | B2 * | 2/2019 | Mahler | C08J 9/144 |
| RE49,849 | E * | 2/2024 | Rao | C07C 17/06 |
| 2005/0228202 | A1 * | 10/2005 | Nappa et al. | 570/161 |
| 2006/0030744 | A1 | 2/2006 | Mukhopadhyay et al. | |
| 2006/0094911 | A1 | 5/2006 | Rao et al. | |
| 2006/0106263 | A1 | 5/2006 | Miller et al. | |
| 2020/0172455 | A1 | 6/2020 | Rao et al. | |

FOREIGN PATENT DOCUMENTS

| | | | | |
|---|---|---|---|---|
| JP | 10309464 | | 11/1998 | |
| JP | 10309464 | A | 11/1998 | |
| WO | 97/05089 | | 2/1997 | |
| WO | 9705089 | A1 | 2/1997 | |
| WO | 98/42645 | | 10/1998 | |
| WO | 9842645 | A1 | 10/1998 | |
| WO | WO-2007002625 | A2 * | 1/2007 | A61P 23/02 |
| WO | 2007056194 | A1 | 5/2007 | |
| WO | 2007079431 | A2 | 7/2007 | |
| WO | 2008024508 | A1 | 2/2008 | |
| WO | 2008/054781 | A1 | 5/2008 | |

OTHER PUBLICATIONS

Satterfield, Charles N. Heterogeneous Catalysis in Industrial Practice, 2nd edition, 1991, pp. 87-112, McGraw-Hill, New York.

Haszeldine, R. N., Fluoro-olefins. Part II. Synthesis and Reactions of Some 3,3,3-Trihalogenopropenes, Journal of Chemical Sciety, 1953, pp. 3371-3378.

Haszeldine, R. N., The Addition of Free Radicals to Unsaturated Systems. Part I. The Direction of Radical Addition to 3:3:3-Trifluoropropene., Journal of Chemical Society, 1952, pp. 2504-2513.

Mcbee, E.T. et al., Journal of American Society, Apr. 1947, pp. 944-947, vol. 69.

Hawley's Condensed Chemical Dictionary, 13th Ed. Revised R.J. Lewis, Sr., 1997, pp. 20, 222, 239, John Wiley & Sons, Inc., New York.

Henne, A. L. et al., Influence of a CF3 Group on an Adjacent Double Bond, Journal of Chemical Society, 72, 1950, p. 3369.

Joyce, R. M. et al., Free Radical-initiated Reaction of Ethylene with Carbon Tetrachloride, Jul. 1948, pp. 2529-2532.

Knunyants, I. L. et al., Reactions of Fluoro Olefines Presentation 13. Catalytic Hydrogenation of Perfluoro Olefins, Bulletin of the Academy of Sciences of the USSR, Division of Chemical Sciences, 1960, Moscow, Russia.

Kotz et al., Chemistry & Chemical Reactivity, 2003, p. 607, 5th Edition, Thomson Learning, Inc.

Petition for Inter Partes Review filed Sep. 18, 2020 for U.S. Pat. No. 8,633,340 (Issued Jan. 21, 2014).

PTAB Interference Decision Entered Nov. 26, 2019, Patent Interference No. 106,099.

Reply Brief for Appellants Filed Oct. 6, 2020, Patent Interference No. 106,099.

John W. Smith Notice of Priority Statement Filed Oct. 26, 2018, Patent Interference No. 106,099.

Heterogeneous Catalysis in Industrial Practice, 2nd Edition (McGraw-Hill, New York, 1991), Author: Satterfield, pp. 87-112.

Haszeldine—Journal of Chemical Society (1951), pp. 2495-2504.

* cited by examiner

PROCESSES FOR THE PRODUCTION OF FLUOROPROPANES AND HALOPROPENES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE TO RELATED APPLICATIONS*

This application [represents] *is a Reissue of U.S. Pat. No. 8,318,992, issued Nov. 27, 2012, which claims priority of U.S. patent application Ser. No. 12/444,462* a national filing under 35 U.S.C. 371 of International Application No. PCT/US2007/022995 filed Oct. 31, 2007, and claims priority of U.S. Provisional Application No. 60/855,538, filed Oct. 31, 2006*, and this application is also a reissue continuation of U.S. patent application Ser. No. 14/552,613, filed on Nov. 25, 2014, which is a Reissue of U.S. Pat. No. 8,318,992, issued Nov. 27, 2012, which claims priority to U.S. patent application Ser. No. 12/442,462 which is a national filing under 35 U.S.C. 371 of International Application No. PCT/US2007/022995 filed Oct. 31, 2006.*

FIELD OF THE INVENTION

The present invention relates to processes for the production of 1,1,1,2,2-pentafluoropropane, 2,3,3,3-tetrafluoro-1-propene, 1,1,1,3,3-pentafluoropropane, 1,3,3,3-tetrafluoro-1-propene, 2-chloro-3,3,3-trifluoro-1-propene and/or 1-chloro-3,3,3-trifluoro-1-propene.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

1,1,1,3,3-Pentafluoropropane ($CF_3CH_2CHF_2$ or HFC-245fa), a refrigerant and blowing agent, may be prepared by fluorination of 1,1,1,3,3-pentachloropropane ($CCl_3CH_2CHCl_2$ or HCC-240fa) in the liquid phase (see for example, U.S. Pat. No. 6,291,730).

1,1,1,2,2-Pentapropane ($CF_3CF_2CH_3$ or HFC-245cb), useful as a refrigerant and blowing agent has been prepared by the addition of methyl fluoride to tetrafluoroethylene in the presence of antimony pentafluoride as disclosed in U.S. Pat. No. 6,184,426.

2,3,3,3-Tetrafluoro-1-propene ($CF_3CF{=}CH_2$ or HFC-1234yf), useful as a refrigerant and as a polymer intermediate has been prepared by fluorination of $CH_3CF_2CCl_3$ over chromium oxide as disclosed by Rausch in U.S. Pat. No. 2,996,555.

1-Chloro-3,3,3-trifluoro-1-propene ($CF_3CH{=}CHCl$ or HCFC-1233zd) is useful as a chemical intermediate and may be prepared by fluorination of HCC-240fa as disclosed in U.S. Pat. No. 6,013,846.

1,3,3,3-Tetrafluoro-1-propene ($CF_3CH{=}CHF$ or HFC-1234ze) useful as a refrigerant has been prepared by dehydrofluorination of HFC-245fa using a strong base in aqueous or alcoholic solution or by means of chromium-containing catalyst in the presence of oxygen at elevated temperature as disclosed in U.S. Pat. No. 6,124,510, and from HCFC-1233zd as disclosed in U.S. Pat. No. 5,895,825. HFC-1234ze has also been prepared from HCC-240fa as disclosed in U.S. Pat. No. 6,111,150.

2-Chloro-3,3,3-trifluoro-1-propene ($CF_3CCl{=}CH_2$ or HCFC-1233xf) is useful as an intermediate and as a monomer for polymers. HCFC-1233xf has been prepared by dehydrochlorination of 1,2-dichloro-3,3,3-trifluoropropane using potassium hydroxide as described by Haszeldine in Journal of the Chemical Society (1951) pages 2495 to 2504.

There is a need for processes for the manufacture of a compound from the group HCFC-1233xf, HFC-245fa, HFC-245cb, HFC-1234ze, HCFC-1233zd, and HFC-1234yf, where other compounds of the group are also produced from common halogenated hydrocarbon starting materials and those other compounds can, if desired, also be recovered.

SUMMARY OF THE INVENTION

The present invention provides a process for making at least one product compound selected from the group consisting of $CF_3CF_2CH_3$, $CF_3CF{=}CH_2$ and $CF_3CCl{=}CH_2$. The process comprises reacting at least one starting material selected from the group consisting of halopropanes of the formula $CX_3CH_2CH_2X$, halopropenes of the formula $CX_3CH{=}CH_2$, and halopropenes of the formula $CX_2{=}CHCH_2X$ wherein each X is independently selected from the group consisting of F and Cl, with HF and $Cl_2$ in a reaction zone, optionally in the presence of a chlorofluorination catalyst, to produce a product mixture comprising HF, HCl, $CF_3CF_2CH_3$, $CF_3CF{=}CH_2$ and $CF_3CCl{=}CH_2$, wherein the molar ratio of HF to total amount of starting material fed to the reaction zone is at least stoichiometric and wherein the molar ratio of $Cl_2$ to total amount of starting material fed to the reaction zone is 2:1 or less; and recovering said at least one product compound from the product mixture.

The present invention also provides a process for making at least one product compound selected from the group consisting of $CF_3CH_2CHF_2$, $CF_3CH{=}CHF$ and $CF_3CH{=}CHCl$. The process comprises reacting at least one starting material selected from the group consisting of halopropenes of the formula $CX_3CH{=}CH_2$ and halopropenes of the formula $CX_2{=}CHCH_2X$ wherein each X is independently selected from the group consisting of F and Cl, with HF and $Cl_2$ in a reaction zone, optionally in the presence of a chlorofluorination catalyst, to produce a product mixture comprising HF, HCl, $CF_3CH_2CHF_2$, $CF_3CH{=}CHF$ and $CF_3CH{=}CHCl$, wherein the molar ratio of HF to total amount of starting material fed to the reaction zone is at least stoichiometric and wherein the molar ratio of $Cl_2$ to total amount of starting material fed to the reaction zone is 2:1 or less; and recovering said at least one product compound from the product mixture.

DETAILED DESCRIPTION

The term "starting material", as used herein, means halopropanes or halopropenes which react with hydrogen fluoride (HF) and chlorine ($Cl_2$) in a reaction zone in the embodiments of this invention. As indicated above, for certain processes of this invention the starting material is selected from the group consisting of halopropanes of the formula $CX_3CH_2CH_2X$, halopropenes of the formula $CX_3CH{=}CH_2$ and halopropenes of the formula $CX_2{=}CHCH_2X$, wherein each X is independently selected from the group consisting of F and Cl; and for certain other processes of this invention the starting material is selected from the group consisting of halopropenes of the formula $CX_3CH{=}CH_2$ and halopropenes of the formula $CX_2{=}CHCH_2X$, wherein each X is independently selected from the group consisting of F and Cl.

The processes of this invention use a molar ratio of HF to the total amount of starting material that is at least stoichiometric. The stoichiometric ratio is determined by subtracting the weighted average of the number of fluorine substituents in the starting material(s) from the weighted average of the number of fluorine substituents in the desired product(s). For example, for producing a $C_3H_3F_5$ isomer from $C_3H_4Cl_4$, the stoichiometric ratio of HF to $C_3H_4Cl_4$ is 5:1. As another example, for producing a 1:1 mixture of HFC-245cb to HFC-1234yf from $CF_3CH{=}CH_2$, the stoichiometric ratio of HF to $CF_3CH{=}CH_2$ is 1.5:1.

Certain compounds produced by the processes of this invention may exist as one of two configurational isomers. For example, HFC-1234ze and HCFC-1233zd may each exist as E- or Z-isomers. As used herein HFC-1234ze refers to the isomers, E-HFC-1234ze or Z-HFC-1234ze, as well as any combinations or mixtures of such isomers; and HCFC-1233zd as used herein refers to the isomers, E-HCFC-1233zd or Z-HCFC-1233zd, as well as any combinations or mixtures of such isomers.

As indicated above, the present invention provides a process that involves producing a product mixture comprising at least one product compound selected from the group consisting of HFC-245cb, HFC-1234yf and HCFC-1233xf using at least one starting material selected from the group consisting of halopropanes of the formula $CX_3CH_2CH_2X$, halopropenes of the formula $CX_3CH{=}CH_2$ and halopropenes of the formula $CX_2{=}CHCH_2X$. Of note are embodiments of this process wherein HFC-1234yf is recovered. Additional HFC-1234yf may be obtained by dehydrofluorination of HFC-245cb from the product mixture. Also of note are embodiments of this process wherein HCFC-1233xf from the product mixture is fluorinated to produce at least one of HFC-1234yf and HFC-245cb.

The product mixture may also comprise HFC-1234ze. The HFC-1234ze may be recovered. The product mixture may further comprise HCFC-1233zd. HFC-1234ze and HFC-245fa may also be obtained by fluorination of HCFC-1233zd from the product mixture.

The product mixture may also comprise HFC-245fa. The HFC-245fa may be recovered. The HFC-245fa may also be dehydrofluorinated to produce HFC-1234ze.

The product mixture may further comprise HFC-1234ze. A mixture of HFC-245cb and HFC-1234ze may be recovered and further reacted with HF in the liquid phase under fluorination conditions in the presence of a fluorination catalyst to produce a mixture comprising HFC-245fa and HFC-245cb. Alternatively, a mixture of HFC-245cb and HFC-1234ze may be recovered and further reacted under dehydrofluorination conditions in the presence of a dehydrofluorination catalyst to produce a mixture comprising HFC-1234ze and HFC-1234yf.

HFC-245fa, HFC-1234ze and/or HCFC-1233zd may also be present in the product mixture. HFC-245cb, HFC-1234yf, and HCFC-1233xf from the product mixture together with HFC-245fa (if present), HFC-1234ze (if present) and HCFC-1233zd (if present) may be further reacted with HF in the liquid phase under fluorination conditions in the presence of a fluorination catalyst to produce a mixture comprising HFC-245fa and HFC-245cb. The HFC-245fa and HFC-245cb from the mixture may be dehydrofluorinated (individually or as a mixture) to produce both HFC-1234ze and HFC-1234yf which may be recovered. See for example, U.S. Patent Application Publication US2006/0106263(A1), which is hereby incorporated herein by reference.

HCFC-1233zd and HFC-245fa may also be present in the product mixture; and HCFC-1233xf, HCFC-1233zd, and HFC-245fa from the product mixture may be further reacted with HF in the liquid phase under fluorination conditions in the presence of a fluorination catalyst to produce a mixture comprising $CF_3CH_2CHF_2$ and $CF_3CF_2CH_3$.

As indicated above, the present invention also provides a process that involves producing a product mixture comprising HFC-245fa, HFC-1234ze, and HCFC-1233zd using at least one starting material selected from the group consisting of halopropenes of the formula $CX_3CH{=}CH_2$ and halopropenes of the formula $CX_2{=}CHCH_2X$. Of note are embodiments of the process wherein HFC-1234ze is recovered. Additional HFC-1234ze may be obtained by dehydrofluorination of HFC-245fa from the product mixture. Also of note are embodiments of this process wherein HCFC-1233zd from the product mixture is fluorinated to produce at least one of HFC-1234ze and HFC-245fa.

Also of note are processes wherein HFC-245fa is recovered.

Also of note are processes wherein the product mixture further comprises HFC-1234yf and wherein HFC-1234yf from the product mixture is recovered.

The product mixture may further comprise HFC-245cb. A mixture of HFC-245cb and HFC-1234ze may be recovered and further reacted with HF in the liquid phase under fluorination conditions in the presence of a fluorination catalyst to produce a mixture comprising HFC-245fa and HFC-245cb. Alternatively, a mixture of HFC-245cb and HFC-1234ze may be recovered and further reacted under dehydrofluorination conditions in the presence of a dehydrofluorination catalyst to produce a mixture comprising HFC-1234ze and HFC-1234yf.

HFC-245cb, HFC-1234yf and/or HCFC-1233xf may also be present in the product mixture. HFC-245fa, HFC-1234ze and HCFC-1233zd from the product mixture together with HFC-245cb (if present), HFC-1234yf (if present) and HCFC-1233xf (if present) may be further reacted with HF in the liquid phase under fluorination conditions in the presence of a fluorination catalyst to produce a mixture comprising HFC-245fa and HFC-245cb. The HFC-245fa and HFC-245cb from the mixture may be dehydrofluorinated (individually or as a mixture) to produce both HFC-1234ze and HFC-1234yf which may be recovered. See for example, U. S. Patent Application Publication US200610106263(A1).

HCFC-1233xf may also be present in the product mixture; and HCFC-1233xf, HCFC-1233zd, and HFC-245fa from the product mixture may be further reacted with HF in the liquid phase under fluorination conditions in the presence of a fluorination catalyst to produce a mixture comprising $CF_3CH_2CHF_2$ and $CF_3CF_2CH_3$.

Suitable halopropane starting materials of the formula $CX_3CH_2CH_2X$ include $CF_3CH_2CH_2F$ (HFC-254fb), $CF_3CH_2CH_2Cl$ (HCFC-253fb), $CClF_2CH_2CH_2Cl$ (HCFC-252fc), $CCl_2FCH_2CH_2Cl$(HCFC-251fb) and $CCl_3CH_2CH_2Cl$ (HCC-250fb). Preferred is HCC-250fb.

Suitable halopropene starting materials of the formula $CX_3CH{=}CH_2$ include $CF_3CH{=}CH_2$ (HFC-1243zf), $CClF_2CH{=}CH_2$ (HCFC-1242zf), $CCl_2FCH{=}CH_2$ (HCFC-1241zf), and $CCl_3CH{=}CH_2$ (HCC-1240zf). Preferred is HFC-1243zf.

Suitable halopropene starting materials of the formula $CX_2{=}CHCH_2X$ include $CCl_2{=}CHCH_2Cl$ (HCC-1240za).

HCC-250fb is a readily available starting material that can be prepared by the reaction of ethylene with carbon tetrachloride as disclosed in International Patent Application No. WO 97/05089, which is incorporated herein by reference. HCC-250fb may be converted to HFC-1243zf by reaction with HF in vapor phase as disclosed in U.S. Pat. No. 6,329,559, which is incorporated herein by reference. HCC-1240za may be prepared by reaction of 1,1,1,3-tetrachloropropane with ferric chloride as disclosed by Fujimori, et. al. in Japanese Kokai 49066613.

The reaction may be carried out in the liquid or vapor phase. For liquid phase embodiments of the invention, the reaction of starting materials with HF and $Cl_2$ may be conducted in a liquid-phase reactor operating in batch, semi-batch, semi-continuous, or continuous modes. In the batch mode, starting materials, $Cl_2$, and HF are combined in an autoclave or other suitable reaction vessel and heated to the desired temperature.

Preferably, this reaction is carried out in semi-batch mode by feeding $Cl_2$ to a liquid-phase reactor containing HF and starting materials or by feeding starting materials and $Cl_2$ to a liquid-phase reactor containing HF, or by feeding $Cl_2$ to a mixture containing HF and reaction products formed by initially heating starting materials and HF. Alternatively, HF and $Cl_2$ may be fed to a liquid-phase reactor containing a mixture of starting materials and reaction products formed by reacting HF, $Cl_2$, and starting materials. In another embodiment of the liquid-phase process, HF, $Cl_2$, and starting materials may be fed concurrently in the desired stoichiometric ratio to the reactor containing a mixture of HF and reaction products formed by reacting HF, $Cl_2$, and starting materials.

Suitable temperatures for the reaction of HF and $Cl_2$ with starting materials in the liquid-phase reactor are from about 80° C. to about 180° C., preferably from about 100° C. to about 150° C. Higher temperatures typically result in greater conversion of the starting materials.

A suitable molar ratio of HF to total amount of starting materials fed to the liquid-phase reactor is at least stoichiometric and is typically from about 5:1 to about 100:1. Of note are embodiments wherein the molar ratio of HF to starting material is from about 8:1 to about 50:1. A suitable molar ratio of $Cl_2$ to total amount of starting materials fed to the liquid-phase reactor is from about 1:1 to about 2:1.

The reactor pressure in the liquid-phase process is not critical and in batch reactions is usually the autogenous pressure of the system at the reaction temperature. The pressure of the system increases as hydrogen chloride is formed by replacement of hydrogen substituents by chlorine, and by replacement of chlorine substituents by fluorine in the starting materials and intermediate reaction products. In a continuous process it is possible to set the pressure of the reactor in such a way that the lower boiling products of the reaction, such as HCl, $CF_3CF{=}CH_2$, E/Z-$CF_3CH{=}CHF$, and $CF_3CF_2CH_3$, are vented from the reactor, optionally through a packed column or condenser. In this manner, higher boiling intermediates remain in the reactor and the volatile products are removed. Typical reactor pressures are from about 20 psig (239 kPa) to about 1,000 psig (6,994 kPa).

In embodiments of the invention in which the reaction is conducted using a liquid-phase process, catalysts which may be used include carbon, $AlF_3$, $BF_3$, $FeCl_{3-a}F_a$ (where a=0 to 3), $FeX_3$ supported on carbon, $SbCl_{3-a}F_a$, $AsF_3$, $MCl_{5-b}F_b$ (where b=0 to 5 and M=Sb, Nb, Ta, or Mo), and $M'Cl_{4-c}F_c$ (where c=0 to 4, and M'=Sn, Ti, Zr, or Hf). Preferred catalysts for the liquid phase process are $MCl_{5-b}F_b$ (where b=0 to 5 and M=Sb, Nb, or Ta).

Preferably, the reaction of HF and $Cl_2$ with starting materials is carried out in the vapor phase. Typically a heated reactor is used. A number of reactor configurations are possible including horizontal or vertical orientation of the reactor as well as the sequence of reaction of the starting materials with HF and $Cl_2$. In one embodiment of the invention, the starting materials may be initially vaporized and fed to the reactor as gases.

In another embodiment of the invention, starting materials may be contacted with HF, optionally in the presence of $Cl_2$, in a pre-reactor prior to reaction in the vapor-phase reactor. The pre-reactor may be empty, but is preferably filled with a suitable packing such as Monel™ or Hastelloy™ nickel alloy turnings or wool, or other material inert to HCl and HF which allows efficient mixing of starting materials and HF vapor.

Suitable temperatures for the pre-reactor for this embodiment of the invention are from about 80° C. to about 250° C., preferably from about 100° C. to about 200° C. Temperatures greater than about 100° C. result in some conversion of the starting materials to compounds having a higher degree of fluorination. Higher temperatures result in greater conversion of the starting materials entering the reactor and a greater degree of fluorination in the converted compounds. Under these conditions, for example, a mixture of HF, $Cl_2$, and HCC-250fb is converted to a mixture containing predominantly HFC-1243zf and HCFC-243db ($CF_3CHClCH_2Cl$) and a mixture of HF, $Cl_2$, and HFC-1243zf is converted to a mixture containing predominantly HCFC-243db and HCFC-244db ($CF_3CHClCH_2F$).

The degree of fluorination reflects the number of fluorine substituents that replace chlorine substituents in the starting materials and their chlorinated products. For example, HCFC-253fb represents a higher degree of fluorination than HCC-250fb and HFC-1243zf represents a higher degree of fluorination than HCC-1240zf.

The molar ratio of HF to the total amount of starting material(s) in the pre-reactor is typically from about the stoichiometric ratio of HF to the total amount of starting material to about 50:1. Preferably, the molar ratio of HF to the total amount of starting material in the pre-reactor is from about twice the stoichiometric ratio of HF to the total amount of starting material to about 30:1. In one embodiment of the invention, the preferred molar ratio of HF to the total amount of starting materials is present in the pre-reactor, and no additional amount of HF is added to the vapor-phase reaction zone.

In another embodiment of the invention, the starting materials may be contacted with $Cl_2$ in a pre-reactor, optionally in the presence of HF, prior to reaction in the vapor-phase reactor.

Suitable temperatures for the pre-reactor for this embodiment of the invention are from about 80° C. to about 250° C., preferably from about 100° C. to about 200° C. Under these conditions, at least a portion of $CX_3CH_2CH_2X$ is converted to $CX_3CHClCH_2X$, at least a portion of $CX_3CH{=}CH_2$ is converted to $CX_3CHClCH_2Cl$, and at least a portion of $CX_2{=}CHCH_2X$ is converted to $CX_2ClCHClCH_2X$. Higher temperatures typically result in a higher degree of halogenation of the starting material.

The degree of halogenation reflects the total number of halogen substituents (chlorine plus fluorine) in a halopropane and/or halopropene product. For example, HFC-245cb has a higher degree of halogenation (i.e., 5) than does HCC-250fb (i.e., 4); and HFC-1234yf has a higher degree of halogenation (i.e., 4) than does HFC-1243zf (i.e., 3). The preferred degree of halogenation in the halopropane products in the process of this invention is five. The preferred degree of halogenation of halopropene products in the process of this invention is four.

The molar ratio of $Cl_2$ to the total amount of the starting materials is typically from about 0.5:1 to about 2:1. Preferably the molar ratio of $Cl_2$ to the total amount of the starting materials is from about 1.1:1 to about 1:1.

In a preferred embodiment of the invention, the starting materials are vaporized, optionally in the presence of HF, and fed to a pre-reactor or to a vapor-phase reactor along with HF and $Cl_2$.

Suitable temperatures for the vapor-phase reaction of this invention are from about 120° C. to about 500° C. Temperatures of from about 250° C. to about 350° C. favor the formation of HFC-1234yf and HFC-245cb. Temperatures of from about 350° C. to about 450° C. favor the formation of HFC-1234ze, HFC-245fa, and HCFC-1233zd. At temperatures of from about 250° C. to about 450° C., some HCFC-1233xf is also produced. Higher temperatures result in greater conversion of starting materials and higher degrees of fluorination and halogenation in the converted compounds.

Suitable reactor pressures for the vapor-phase reactor may be from about 1 to about 30 atmospheres. A pressure of about 15 to about 25 atmospheres may be advantageously employed to facilitate separation of HCl from other reaction products, and the suitable reaction time may vary from about 1 to about 120 seconds, preferably from about 5 to about 60 seconds.

The molar ratio of HF to the total amount of starting material(s) for the vapor-phase reaction is typically from about the stoichiometric ratio of HF to the total amount of starting material to about 50:1 and preferably from about 10:1 to about 30:1.

Preferably a catalyst is used in the reaction zone for the vapor-phase reaction of HF and $Cl_2$ with starting materials. Chlorofluorination catalysts which may be used in the vapor phase reaction of the invention include carbon; graphite; alumina; fluorided alumina; aluminum fluoride; alumina supported on carbon; aluminum fluoride supported on carbon; fluorided alumina supported on carbon; magnesium fluoride supported on aluminum fluoride; metals (including elemental metals, metal oxides, metal halides, and/or other metal salts); metals supported on aluminum fluoride; metals supported on fluorided alumina; metals supported on alumina; and metals supported on carbon; mixtures of metals.

Suitable metals for use as catalysts (optionally supported on alumina, aluminum fluoride, fluorided alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). Preferably when used on a support, the total metal content of the catalyst will be from about 0.1 to about 20 percent by weight based on the total weight of the catalyst; typically from about 0.1 to about 10 percent by weight based on the total weight of the catalyst.

Suitable chlorofluorination catalysts for the vapor-phase reactions in this invention include chromium-containing catalysts including chromium(III) oxide ($Cr_2O_3$); $Cr_2O_3$ with other metals such as magnesium halides or zinc halides supported on $Cr_2O_3$; chromium(III) halides supported on carbon; mixtures of chromium and magnesium (including elemental metals, metal oxides, metal halides, and/or other metal salts) optionally supported on graphite; and mixtures of chromium and other metals (including elemental metals, metal oxides, metal halides, and/or other metal salts) optionally supported on graphite, alumina, or aluminum halides such as aluminum fluoride.

Chromium-containing catalysts are well known in the art. They may be prepared by either precipitation methods or impregnation methods as generally described by Satterfield on pages 87-112 in Heterogeneous Catalysis in Industrial Practice, $2^{nd}$ edition (McGraw-Hill, New York, 1991).

Of note are chlorofluorination catalysts that comprise at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms, and crystalline alpha-chromium oxide where from about 0.05 atom % to about 6 atom % of the chromium atoms in the alpha-chromium oxide lattice are replaced by trivalent cobalt atoms which has been treated with a fluorinating agent. These catalysts, including their preparation, have been disclosed in U. S. Patent Application Publication US2005/0228202 which is incorporated herein by reference in its entirety.

Optionally, the metal-containing catalysts described above can be pretreated with HF. This pretreatment can be accomplished, for example, by placing the metal-containing catalyst in a suitable container, and thereafter, passing HF over the metal-containing catalyst. In one embodiment of this invention, such container can be the reactor used to perform the chlorofluorination reaction in this invention. Typically, the pretreatment time is from about 15 to about 300 minutes, and the pretreatment temperature is from about 200° C. to about 450° C.

In one embodiment of this invention, the product mixture comprises HFC-245cb, HFC-245fa, HFC-1234yf, HFC-1234ze, HCFC-1233zd and HCFC-1233xf.

Halopropane by-products that may be formed in the chlorofluorination reactions of this invention having higher degrees of halogenation and/or fluorination than pentafluoropropanes include $CF_3CCl_2CF_3$ (CFC-216aa), $CF_3CClFCClF_2$ (CFC-216ba), $CF_3CClFCF_3$ (CFC-217ba), $CF_3CF_2CClF_2$ (CFC-217ca), $CF_3CHFCF_3$ (HFC-227ea), $CF_3CF_2CHF_2$ (HFC-227ca), $CF_3CClFCHF_2$ (HCFC-226ba), $CF_3CF_2CHClF$ (HCFC-226ca), $CF_3CHClCF_3$ (HCFC-226da), $CF_3CCl_2CHF_2$ (HCFC-225aa), $CF_3CClFCHClF$ (HCFC-225ba), $CF_3CF_2CHCl_2$ (HCFC-225ca), $CF_3CCl_2CClF_2$ (CFC-215aa), $CF_3CClFCCl_2F$ (CFC-215bb), $CF_3CCl_2CCl_2F$ (HCFC-214ab), $CF_3CCl_2CHClF$ (HCFC-224aa), and $CF_3CClFCHCl_2$ (HCFC-224ba).

Halopropene by-products that may be formed in the chlorofluorination reactions of this invention having a higher degree of halogenation than tetrafluoropropenes include $CF_3CCl{=}CHCl$ (HCFC-1223xd).

In cases where the product mixture produced by the processes of this invention comprises (i) product compounds HFC-245cb, HFC-245fa, HFC-1234yf, HFC-1234ze, HCFC-1233zd and HCFC-1233xf, (ii) HF, HCl, and $Cl_2$, (iii) higher boiling by-products such as $CF_3CHClCH_2Cl$, $CF_3CHClCH_2F$ and (iv) chlorinated by-products such as $C_3HCl_3F_4$, $C_3HCl_2F_5$, $C_3HClF_6$, $C_3Cl_3F_5$, and $C_3Cl_2F_6$, the separation steps (a) through (e) may be employed to recover the product compounds from such a product mixture.

In separation step (a), the product mixture may be delivered to a distillation column to separate HCl and $Cl_2$ from the product mixture.

In separation step (b), the product mixture from separation step (a) may be delivered to one or more distillation columns to separate the azeotropic composition of HFC-1234yf and HF from the rest of the product mixture. The recovered azeotropic composition of HFC-1234yf and HF may be further separated into individual components by using procedures similar to those described in U. S. Patent Application Publication US2006/0106263(A1).

In separation step (c), the product mixture from separation step (b) may be delivered to one or more distillation columns in which HF, HFC-245cb, HFC-1234ze, HCFC-1233xf, HCFC-1233zd, and HFC-245fa are recovered from the top of the distillation column, and the higher boiling by-products such as $CF_3CHClCH_2Cl$, $CF_3CHClCH_2F$ and the chlorinated by-products such as $C_3HCl_3F_4$, $C_3HCl_2F_5$, $C_3HClF_6$, $C_3Cl_3F_5$, and $C_3Cl_2F_6$ are removed from the bottom of the distillation column. The higher boiling by-products such as $CF_3CHClCH_2Cl$ and $CF_3CHClCH_2F$ may be further separated from the chlorinated by-products, e.g. by distillation, and may be recycled back to the vapor-phase chlorofluorination reactor.

In separation step (d), the product mixture comprising HF, HFC-245cb, HFC-1234ze, HCFC-1233xf, HCFC-1233zd and HFC-245fa, which is recovered from the top of the distillation column in separation step (c), may be delivered to one or more distillation columns to recover the azeotropic composition of HFC-245cb/HF and the azeotropic composition of HFC-1234ze/HF from the top of the distillation column. The recovered HFC-245cb/HF and HFC-1234ze/HF azeotropic compositions may then be further separated into individual components by using procedures similar to those described in U.S. Patent Application Publication US2006/0106263(A1).

In separation step (e), the product mixture comprising HCFC-1233xf, HCFC-1233zd and HFC-245fa and any HF recovered from the bottom of the distillation column in separation step (d) may be delivered to a distillation column to separate the HCFC-1233xf, HCFC-1233zd and HFC-245fa. The HCFC-1233xf can be fluorinated to produce at least one of HFC-245cb and HFC-1234yf. The HCFC-1233zd can be fluorinated to produce at least one of HFC-245fa and HFC-1234ze.

As indicated above, in certain embodiments of this invention, the mixture of HF, HFC-245cb and HFC-1234ze, made according to the process of the invention is contacted with additional HF in a liquid-phase fluorination reactor, optionally in the presence of a liquid-phase fluorination catalyst to give a mixture of HF, HFC-245cb and HFC-245fa. The mixture of HF, HFC-245cb, and HFC-245fa is then separated into the individual components by using procedures similar to those described in U.S. Patent Application Publication US200610106263(A1). Suitable fluorination catalysts for these embodiments may be selected from those described for the liquid-phase embodiment of the chlorofluorination reactor described herein. The mole ratio of HF to HFC-245cb and HFC-1234ze in these embodiments is typically from about 5:1 to about 100:1, and is preferably from about 10:1 to about 40:1 based on the amount of HFC-1234ze in the mixture. Suitable temperatures for these embodiments of the invention are within the range of from about 30° C. to about 180° C., preferably from about 50° C. to about 150° C. Suitable reactor pressures for these embodiments are usually the autogenous pressures at the reactor temperatures. The pressure may be in the range of from about 1 to about 30 atmospheres.

As indicated above, in certain embodiments of this invention, a mixture of HF, HFC-245cb and HFC-1234ze, made according to the processes of this invention, may be delivered to a reaction zone containing a dehydrofluorination catalyst (optionally after removal of the HF). Conditions in the reaction zone are chosen to be suitable for conversion of HFC-245cb to HFC-1234yf. The products leaving the reactor, comprising HFC-1234ze and HFC-1234yf are separated by techniques known to the art. Catalysts suitable for these embodiments of the invention and suitable operating conditions are disclosed in U.S. Pat. No. 5,396,000 the teachings of which are herein incorporated by reference. Preferably, the dehydrofluorination catalyst comprises aluminum fluoride or fluorided alumina or trivalent chromium oxide. Reaction temperatures suitable for these embodiments are from about 150° C. to about 500° C. Contact times in the reaction zone for these embodiments are typically from about 1 second to about 500 seconds.

As indicated above, in certain embodiments of this invention, a mixture of HCFC-1233xf, HCFC-1233zd, and HFC-245fa made according to the process of the invention, is reacted with HF in a liquid-phase fluorination reactor in the presence of a liquid-phase fluorination catalyst to give a mixture of HF, HFC-245cb and HFC-245fa. The conditions of the fluorination are similar to those described for the mixture of HFC-1234ze and HFC-245cb above. The mixture of HF, HFC-245cb, and HFC-245fa is then optionally delivered to a distillation column to separate the two pentafluoropropanes and azeotropic HF by using procedures similar to those described in U.S. Patent Application Publication US2006/0106263(A1).

As noted above, HFC-245cb, made according to the processes of this invention, may be dehydrofluorinated to produce HFC-1234yf, and HFC-245fa, made according to the processes of this invention, may be dehydrofluorinated to produce HFC-1234ze. Typical dehydrofluorination reaction conditions and dehydrofluorination catalysts are disclosed in U.S. Pat. No. 5,396,000, which is herein incorporated by reference. Dehydrofluorination reaction temperatures suitable for this invention are from about 150° C. to about 500° C.; however, higher temperature are desirable for the dehydrofluorination of HFC-245cb. Suitable contact times for these dehydrofluorinations are from about 1 second to about 500 seconds. Preferably, the dehydrofluorination catalyst comprises at least one catalyst selected from the group consisting of aluminum fluoride, fluorided alumina, and trivalent chromium oxide.

As indicated above, in certain embodiments of this invention, a mixture of HFC-245cb, HFC-1234yf, HFC-1234ze, HCFC-1233xf, HCFC-1233zd, and HFC-245fa that are present in the product mixtures made according to the processes of the invention, is reacted with HF in a liquid-phase fluorination reactor in the presence of a liquid-phase fluorination catalyst. The conditions of the fluorination are similar to those described for the mixture of HFC-1234ze and HFC-245cb above. The fluorination catalysts for the above liquid-phase embodiments of the invention may be selected from those described for the liquid-phase embodiment the chlorofluorination reactor described herein.

The amount of HF required for the liquid-phase reaction is determined by the total amount of HFC-1234yf, HFC-1234ze, HCFC-1233xf, and HCFC-1233zd, present in the mixture. The mole ratio of HF to the sum of the moles of HFC-1234yf, HFC-1234ze, HCFC-1233xf, and E/Z-HCFC-1233zd is typically from about the stoichiometric amount (between 1:1 to 2:1) to about 100:1, and is preferably from about 8:1 to about 50:1. Suitable temperatures for these embodiments of the invention are typically within the range of from about 30° C. to about 180° C., preferably from about 50° C. to about 150° C. The resulting mixture of pentafluoropropanes (i.e, HFC-245cb and HFC-245fa) may be then be freed of HF and recovered as individual compounds by techniques known to the art.

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Preparation of 98% Chromium/2% Cobalt Catalyst

A solution of 784.30 g $Cr(NO_3)_3[9(H_2O)]$ (1.96 moles) and 11.64 g $Co(NO_3)_2[6(H_2O)]$ (0.040 mole) was prepared in 2000 mL of deionized water. The solution was treated dropwise with 950 mL of 7.4M aqueous ammonia until the pH reached about 8.5. The slurry was stirred overnight at room temperature and then evaporated to dryness in air at 110-120° C. The dried catalyst was then calcined in air at 400° C. for 24 hours prior to use.

General Procedure for Product Analysis

The following general procedure is illustrative of the method used for analyzing the products of fluorination reactions. Part of the total reactor effluent was sampled on-line for organic product analysis using a gas chromatograph equipped a mass selective detector (GC/MS). The gas chromatography utilized a 20 ft. (6.1 m) long×⅛ in. (0.32 cm) diameter tube containing Krytox® perfluorinated polyether on an inert carbon support. The helium flow was 30 mL/min ($5.0\times10^{-7}$ $m^3$/sec). Gas chromatographic conditions were 60° C. for an initial hold period of three minutes followed by temperature programming to 200° C. at a rate of 6° C./minute.

| LEGEND | |
|---|---|
| 215aa is $CClF_2Cl_2CF_3$ | 216aa is $CF_3CCl_2CF_3$ |
| 216ba is $CClF_2CClFCF_3$ | 217ba is $CF_3CClFCF_3$ |
| 217ca is $CClF_2CF_2CF_3$ | 224aa is $CF_3CCl_2CHClF$ |
| 224ba is $CF_3CClFCHCl_2$ | 225aa is $CHF_2Cl_2CF_3$ |
| 225ba is $CHClFCClFCF_3$ | 226ba is $CF_3CClFCHF_2$ |
| 226ca is $CF_3CF_2CHClF$ | 226da is $CF_3CHClCF_3$ |
| 227ca is $CF_3CF_2CHF_2$ | 233ab is $CF_3CCl_2CH_2Cl$ |
| 235da is $CF_3CHClCHF_2$ | 236fa is $CF_3CH_2CF_3$ |
| 243db is $CF_3CHClCH_2Cl$ | 244db is $CF_3CHClCH_2F$ |
| 245cb is $CF_3CF_2CH_3$ | 245fa is $CF_3CH_2CHF_2$ |
| 1223xd is E- and Z-$CF_3CCl{=}CHCl$ | 1233xf is $CF_3CCl{=}CH_2$ |
| 1233zd is E- and Z-$CHCl{=}CHCF_3$ | 1234ze is E- and Z-$CHF{=}CHCF_3$ |
| 1234yf is $CH_2{=}CFCF_3$ | 1243zf is $CH_2{=}CHCF_3$ |

Examples 1-6

Chlorofluorination of $CF_3CH{=}CH_2$

The 98% chromium/2% cobalt catalyst prepared above (21.4 g, 15 mL, −12 to +20 mesh, (1.68 to 0.84 mm)) was placed in a ⅝" (1.58 cm) diameter Inconel™ nickel alloy reactor tube heated in a fluidized sand bath. The catalyst was pre-fluorinated by treatment with HF as follows. The catalyst was heated from 45° C. to 175° C. in a flow of nitrogen (50 cc/min) over the course of about 1.5 h. HF was then admitted to the reactor at a flow rate of 50 cc/min for 1.3 h at a temperature of 175° C. The reactor nitrogen flow was decreased to 20 cc/min and the HF flow increased to 80 cc/min; this flow was maintained for 0.3 h. The reactor temperature was then gradually increased to 400° C. over 1 h. After this period, the HF and nitrogen flow was stopped and the reactor brought to the desired operating temperature. A flow of HF vapor, $CF_3CH{=}CH_2$, and $Cl_2$ then started through the reactor. Part of the reactor effluent was analyzed by on line GC/MS.

The results of the chlorofluorination of $CF_3CH{=}CH_2$ over the 98/2 Cr/Co catalyst at various operating temperatures and indicated molar ratios of HF, $CF_3CH{=}CH_2$, and $Cl_2$ are shown in Table 1; analytical data is given in units of GC area %. The nominal catalyst bed volume was 15 cc; the contact time (CT) was 15 seconds. Examples 1 and 2 were carried out in the absence of the catalyst.

TABLE 1

Chlorofluorination of HFC-1243zf (Part A)

| Ex. No. | HF/1243/$Cl_2$ Ratio | T, ° C. | 1243zf | 243db | 244db | 1234yf | 245cb | 1233xf |
|---|---|---|---|---|---|---|---|---|
| 1 | 10/1/4 | 140 | 3.0 | 54.2 | 9.8 | 5.7 | 0 | 1.4 |
| 2[a] | 10/1/1 | 140 | 31.3 | 46.2 | 11.8 | 2.8 | 0 | 1.5 |
| 3[b] | 10/1/1 | 300 | 5.9 | 0 | 0 | 5.9 | 22.2 | 30.7 |
| 4[c] | 10/1/4 | 325 | 0 | 0 | 0 | 0 | 0 | 0 |

TABLE 1-continued

| Chlorofluorination of HFC-1243zf | | | | | | | | |
|---|---|---|---|---|---|---|---|---|
| 5 | 10/1/1 | 350 | 9.1 | 0 | 0 | 11.3 | 11.3 | 25.2 |
| 6 | 10/1/1 | 375 | 12.8 | 0 | 0 | 11.6 | 6.3 | 20.6 |

(Part B)

| Ex. No. | HF/1243/$Cl_2$ Ratio | T, ° C. | 1233zd | 1234ze | 245fa | 1223xd | 233ab | 226ba | 227ca |
|---|---|---|---|---|---|---|---|---|---|
| 1 | 10/1/4 | 140 | 7.7 | — | — | 1.0 | 6.3 | 0 | 0 |
| 2[a] | 10/1/1 | 140 | 1.4 | — | — | 0 | 1.3 | 0 | 0 |
| 3[b] | 10/1/1 | 300 | 4.1 | 2.1 | 1.3 | 20.2 | 0 | 0 | 0 |
| 4[c] | 10/1/4 | 325 | 0 | 0 | 0 | 0 | 0 | 23.8 | 13.9 |
| 5 | 10/1/1 | 350 | 12.4 | 4.7 | 1.9 | 18.1 | 0 | 0.2 | 0 |
| 6 | 10/1/1 | 375 | 17.6 | 6.5 | 2.3 | 16.1 | 0 | 0.2 | 0 |

[a]243db and 244db confirmed by $^1H$ and $^{19}F$ NMR.
[b]245cb and 1233xf confirmed by $^1H$ and $^{19}F$ NMR.
[c]Additional major products were 215aa, 216aa, 216ba, 225aa, 225ba, 226ca, 226da

The invention claimed is:

[1. A process for making at least one product compound selected from the group consisting of $CF_3CF_2CH_3$, $CF_3CF{=}CH_2$ and $CF_3CCl{=}CH_2$, comprising:

reacting at least one starting material selected from the group consisting of halopropanes of the formula $CX_3CH_2CH_2X$, halopropenes of the formula $CX_3CH{=}CH_2$ and halopropenes of the formula $CX_2{=}CHCH_2X$, wherein each X is independently selected from the group consisting of F and Cl, with HF and $Cl_2$ in a reaction zone, optionally in the presence of a chlorofluorination catalyst, to produce a product mixture comprising at least one product compound selected from the group consisting of $CF_3CF_2CH_3$, $CF_3CF{=}CH_2$ and $CF_3CCl{=}CH_2$, wherein the molar ratio of HF to total amount of starting material fed to the reaction zone is at least stoichiometric and wherein the molar ratio of $Cl_2$ to total amount of starting material fed to the reaction zone is 2:1 or less; and recovering said at least one product compound from the product mixture.]

[2. The process of claim 1 wherein $CF_3CF{=}CH_2$ is recovered.]

[3. The process of claim 2 wherein $CF_3CF_2CH_3$ from the product mixture is dehydrofluorinated to produce additional $CF_3CF{=}CH_2$.]

[4. The process of claim 1 wherein $CF_3CCl{=}CH_2$ from the product mixture is fluorinated to produce at least one of $CF_3CF{=}CH_2$ and $CF_3CF_2CH_3$.]

[5. The process of claim 1 wherein the product mixture further comprises $CF_3CH{=}CHF$; and wherein $CF_3CH{=}CHF$ from the product mixture is recovered.]

[6. The process of claim 1 wherein the product mixture further comprises $CF_3CH{=}CHCl$; and wherein $CF_3CH{=}CHCl$ from the product mixture is fluorinated to produce at least one of $CF_3CH{=}CHF$ and $CF_3CH_2CHF_2$.]

[7. The process of claim 1 wherein the product mixture further comprises $CF_3CH_2CHF_2$; and wherein $CF_3CH_2CHF_2$ from the product mixture is recovered.]

[8. The process of claim 1 wherein the product mixture further comprises $CF_3CH_2CHF_2$; and wherein $CF_3CH_2CHF_2$ from the product mixture is dehydrofluorinated to produce $CF_3CH{=}CHF$.]

[9. The process of claim 1 wherein the product mixture further comprises $CF_3CH{=}CHF$; and wherein a mixture of $CF_3CF_2CH_3$ and $CF_3CH{=}CHF$ is recovered and further reacted under dehydrofluorination conditions in the presence of a dehydrofluorination catalyst to produce a mixture comprising $CF_3CH{=}CHF$ and $CF_3CF{=}CH_2$.]

[10. The process of claim 1 wherein the product mixture further comprises $CF_3CH_2CHF_2$ and $CF_3CH{=}CHCl$; and wherein the $CF_3CCl{=}CH_2$, $CF_3CH_2CHF_2$ and $CF_3CH{=}CHCl$ from the product mixture are further reacted with HF in the liquid phase under fluorination conditions in the presence of a fluorination catalyst to produce a mixture comprising $CF_3CH_2CHF_2$ and $CF_3CF_2CH_3$.]

[11. The process of claim 1 wherein the starting material is reacted in the vapor phase in the presence of a chlorofluorination catalyst.]

[12. The process of claim 11 wherein the chlorofluorination catalyst comprises at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms, and crystalline alpha-chromium oxide where from about 0.05 atom % to about 6 atom % of the chromium atoms in the alpha-chromium oxide lattice are replaced by trivalent cobalt atoms which has been treated with a fluorinating agent.]

[13. A process for making at least one product compound selected from the group consisting of $CF_3CF_2CH_3$, $CF_3CF{=}CH_2$ and $CF_3CCl{=}CH_2$, comprising:

reacting at least one starting material selected from the group consisting of halopropanes of the formula $CX_3CH_2CH_2X$, halopropenes of the formula $CX_3CH{=}CH_2$ and halopropenes of the formula $CX_2{=}CHCH_2X$, wherein each X is independently selected from the group consisting of F and Cl, with HF and $Cl_2$ in a reaction zone, in the presence of a chlorofluorination catalyst, to produce a product mixture comprising HF, HCl, $CF_3CF_2CH_3$, $CF_3CF{=}CH_2$ and $CF_3CCl{=}CH_2$, wherein the molar ratio of HF to total amount of starting material fed to the reaction zone is at least stoichiometric and wherein the molar ratio of $Cl_2$ to total amount of starting material fed to the reaction zone is 2:1 or less; and recovering said at least one product compound from the product mixture.]

[14. The process of claim 13 wherein said at least one starting material is halopropenes of the formula $CX_3CH{=}CH_2$.]

[15. The process of claim 14 wherein said at least one starting material is $CF_3CH{=}CH_2$.]

[16. A process for making at least one product compound selected from the group consisting of $CF_3CF_2CH_3$, $CF_3CF{=}CH_2$, $CF_3CCl{=}CH_2$, $CF_3CH_2CHF_2$, $CF_3CH{=}CHF$ and $CF_3CH{=}CHCl$, comprising:

reacting at least one starting material selected from the group consisting of halopropanes of the formula $CX_3CH_2CH_2X$, halopropenes of the formula $CX_3CH{=}CH_2$ and halopropenes of the formula $CX_2{=}CHCH_2X$, wherein each X is independently selected from the group consisting of F and Cl, with HF and $Cl_2$ in a reaction zone, in the presence of a chlorofluorination catalyst, to produce a product mixture comprising $CF_3CF_2CH_3$, $CF_3CF{=}CH_2$, $CF_3CCl{=}CH_2$, $CF_3CH_2CHF_2$, $CF_3CH{=}CHF$ and $CF_3CH{=}CHCl$, wherein the molar ratio of HF to total amount of starting material fed to the reaction zone is at least stoichiometric and wherein the molar ratio of $Cl_2$ to total amount of starting material fed to the reaction zone is 2:1 or less; and recovering said at least one product compound from the product mixture.]

*17. A process for making one or more of $CH_3CH_2CHF_2$ (245fa), $CH_3CF{=}CH_2$ (1234yf), $CH_3CH{=}CHF$ (1234ze), $CF_3CCl{=}CH_2$ (1233xf), and $CF_3CH{=}CHCl$ (1233zd), comprising:*

*reacting at least one halopropene starting material selected from one of $CX_3CH{=}CH_2$ and $CX_2{=}CHCH_2X$, wherein X is independently F or Cl, with HF and $Cl_2$ in a reaction zone, in the presence of a chlorofluorination catalyst to produce a product mixture comprising at least one of $CF_3CH_2CHF_2$ (245fa), $CF_3CF{=}CH_2$ (1234yf), $CF_3CH{=}CHF$ (1234ze), $CF_3CCl{=}CH_2$ (1233xf) and $CF_3CH{=}CHCl{=}CHCl$ (1233zd), wherein the molar ratio of HF to the total amount of starting material fed to the reaction zone is at least stoichiometric, and the molar ratio of $Cl_2$ to total amount of starting material fed to the reaction zone is selected from one of 2:1 or less or from about 0.5:1 to about 2:1.*

*18. The process of claim 17 wherein the reaction is conducted at temperatures between about 250°C and 450°C.*

*19. The process of claim 17 wherein the reaction co-produces $CF_3CH{=}CHF$ (1234ze) and $CF_3CF{=}CH_2$ (1234yf).*

*20. The process of claim 18 wherein the product mixture comprises $CF_3CH{=}CHF$ (1234ze) and $CF_3CF{=}CH_2$ (1234yf).*

*21. The process of claim 18 wherein the product mixture comprises $CF_3CH{=}CHF$ (1234ze) $CF_3CF{=}CH_2$(1234yf) and $CF_3CCl{=}CH_2$(1233xf).*

*22. The process of claim 19 wherein at least $CF_3CH{=}CHF$ (1234ze) is separated and optionally recovered.*

*23. The process of claim 19 wherein at least $CF_3CH{=}CHF$ (1234ze) and $CF_3CF{=}CH_2$ (1234yf) are separated from the product mixture.*

*24. The process of claim 17 wherein the chlorofluorination reaction produces a mixture comprising at least $CF_3CH_2CHF_2$ (245fa), $CF_3CF{=}CH_2$ (1234yf), $CF_3CH{=}CHF$ (1234ze), $CF_3CCl{=}CH_2$(1233xf) and $CF_3CH{=}CHCl$ (1233zd), wherein $CF_3CH{=}CHF$ (1234ze) and $CF_3CH{=}CHCl$ (l233zd) respectively comprise Z-isomer, E-isomer or mixtures thereof.*

*25. The process of any claims 20-22 wherein the $CF_3CH{=}CHF$ (1234ze) is a mixture of E-$CF_3CH{+}CHF$ (1234ze(E)) and Z-$CF_3CH{+}CHF$ (1234ze(Z)).*

*26. The process of any of claims 19-21 wherein the reaction is conducted in the vapor phase.*

*27. The process of claim 17 wherein the product mixture additionally comprises $CF_3CH_2CHF_2$(245fa) and $CF_3CH{=}CHCl$ (1233zd).*

*28. The process of claim 27 wherein the $CF_3CH_2CHF_2$ (245fa) and $CF_3CH{=}CHCl$ (1233zd) in the mixture are converted to $CH_3CH{=}CHF$ (1234ze), wherein $CF_3CH{=}CHF$ (1234ze) comprises at least one of E-$CF_3CH{=}CHF$ (1234ze(E)), $CF_3CH{=}CHF$ (1234ze(Z)), or mixtures thereof.*

*29. The process of claim 17 wherein the mole ratio of HF to the amount of chlorine is at least stoichiometric.*

*30. The process of claim 17 wherein the chlorofluorination catalyst is selected from one of carbon; graphite; alumina; fluorided alumina; aluminum fluoride; alumina supported on carbon; aluminum fluoride supported on carbon; fluorided alumina supported on carbon; magnesium fluoride supported on aluminum fluoride; metals; metals supported on aluminum fluoride; metals supported on fluorided alumina; metals supported on alumina; and metals supported on carbon; and mixtures of metals.*

*31. The process of claim 17 wherein the chlorofluorination catalyst comprises a chromium-containinq catalyst.*

*32. The process of claim 17 wherein the chlorofluorination catalyst comprises at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms.*

*33. The process of claim 32 wherein the chlorofluorination catalyst is pretreated with HF and comprises contact with HF for about 15 to about 300 minutes at a temperature of from between about 200°C to about 450°C.*

*34. The process of claim 27 wherein $CF_3CH_2CHF_2$ (245fa) is dehydrofluorinated to $CF_3CH{=}CHF$ (1234ze), at a temperature from about 150°C to about 500°C.*

*35. The process of claim 17 wherein the starting halopropene comprises one of $CF_3CH{=}CH_2$ (1243zf) or $CCl_2{=}CHCH_2Cl$ (1240za).*

*36. A process for co-producing $CF_3CF{=}CH$ (1234yf) and $CF_3CH{=}CHF$ (1234ze) comprising:*

*reacting at least one halopropene starting material selected from one of $CX_3CH{=}CH_2$ and $CX_2{=}CHCH_2X$, wherein each X is independently F or Cl, with HF and $Cl_2$ in a reaction zone in the presence of a chlorofluorination catalyst to produce a product mixture comprising at least $CF_3CF{=}CH$ (1234yf) and $CF_3CH{=}CHF$ (1234ze); wherein the molar ratio of HF to the total amount of starting material fed to the reaction zone is at least stoichiometric and the molar ratio of $Cl_2$ to total amount of starting material fed to the reaction zone is 2:1 or less.*

*37. A process of claim 36 further producing $CF_3CH_2CHF_2$(245fa) and $CF_3CF_2CH_3$ 1245cb) in the product mixture: and dehydrofluorinating.*

*38. The process of claim 37 wherein the dehydrofluorinating is conducted at temperatures from about 150°C to about 500°C.*

*39. The process of claim 37 wherein the dehydroflourinating occurs in the presence of a dehydrohalogenation catalyst.*

*40. The process of claim 39 wherein the dehydrohalogenation catalyst comprises one of aluminum fluoride, fluorided alumina or a trivalent fluorinated chromium oxide.*

41. The process of claim 36 wherein co-producing $CF_3CF{=}CH_2$(1234yf) and $CF_3CH{=}CHF$ (1234ze) is conducted in the vapor phase.

42. A process for making $CF_3CH{=}CHF$ (1234ze): comprising:

contacting at least one halopropene comprising one of $CF_3CH{=}CH_2$(1243zf) or CCl2=$CHCH_2Cl$ (1240za) with HF and $Cl_2$ in a reaction zone at a temperature of between 300°C and 450°C, in the presence of a chlorofluorination catalyst to produce a product mixture comprising at least $CF_3CH{=}CHF$, wherein the molar ratio of HF to the total amount of starting material fed to the reaction zone is at least stoichiometric, and the molar ratio of $Cl_2$ to total amount of starting material fed to the reaction zone is 2:1 or less.

43. The process of claim 42 wherein the chlorofluorination catalyst comprises at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms.

44. A mixture comprising $CF_3CH{=}CHCl$ (1233zd), $CF_3CH{=}CHF$ (1234ze), $CF_3CH_2CHF_2$(245fa), and at least one of $CF_3CCl{=}CHCl$ (1223xd), $CF_3CF{=}CH_2$ (1234yf) and $CF_3CClFCHF_2$(226ba).

45. A process comprising: reacting one of $CF_3CH{=}CH_2$ (1243zf) and $CCl_2{=}CHCH_2Cl$ (1240za), with HF and $Cl_2$ in a reaction zone, in the presence of a catalyst to produce a product mixture comprising at least $CF_3CH{=}CHF$ (1234ze), wherein the molar ratio of HF to the total amount of the one of $CF_3CH{=}CH_2$(1243zf) and $CCl_2{=}CHCH_2Cl$ (1240za) fed to the reaction zone is at least stoichiometric, and the molar ratio of the $Cl_2$ to total amount of the one of $CF_3CH{=}CH_2$(1243zf) and $CCl_2{=}CHCH_2Cl$ (1240za) fed to the reaction zone is 2:1 or less, and recovering at least $CF_3CH{=}CHF$ (1234ze).

46. A process for making $CF_3CH{=}CHF$ (1234ze), comprising: contacting at least one halopropene comprising one of $CF_3CH{=}CH_2$ (1243zf) or $CCl_2$=CHCH2Cl (1240za) with HF and $Cl_2$ in a liquid phase reaction zone at a temperature of between about 70°C. to about 160°C. in the presence of a catalyst selected from one of AIF, BF, $FeCl_{3-a}F_a$, $FeX_2$ supported on carbon wherein X is a halide, $SbCl_{3-a}F_a$, AsF, $MCl_{5-b}F_b$, $M'Cl_{4-c}F_c$ wherein a=0 to 3, b=0 to 5, c=0 to 4, and M=Sb, Nb, Ta, or Mo and M'=Sn, Ti, Zr, or Hf to produce a product mixture comprisinq at least $CF_3CH{=}CHF$, wherein the molar ratio of HF to the total amount of startinq material fed to the reaction zone is at least stoichiometric, and the molar ratio of $Cl_2$ to total amount of startinq material fed to the reaction zone is 2:1 or less.

47. A process for co-producing $CF_3CH{=}CHF$ (1234ze) and $CF_3CF{=}CH_2$(1234yf), comprising reacting at least one halopropene starting material selected from one of $CX_3CH{=}CH_2$ and $CX_2{=}CHCH_2X$, wherein each X is independently F or Cl, with HF and $Cl_2$ in a reaction zone in the presence of an HF pretreated chlorofluorination catalyst to form a product mixture comprising at least $CF_3CF{=}CH_2$ (1234yf), $CF_3CH{=}CHF$ (1234ze) $CF_3CH_2CHF_2$ (245fa), $CF_3CCl{=}CH_2$ (1233xf) and $CF_3CF_2CH_3$ (245cb); wherein the molar ratio of HF to the total amount of starting material fed to the reaction zone is at least stoichiometric, and the molar ratio of $Cl_2$ to total amount of starting material fed to the reaction zone is 2:1 or less recovering at least $CF_3CF{=}CH_2$(1234yf), $CF_3CH{=}CHF$ (1234ze) $CF_3CH_2CHF_2$(245fa), and $CF_3CF_2CH_3$(245cb) and respectively producing additional $CF_3CF{=}CH_2$(1234yf) and $CF_3CH{=}CHF$ (1234ze) from $CF_3CF_2CH_3$ (245cb) and $CF_3CH_2CHF_2$ (245fa).

48. The process of any of claims 17 or 36 further comprising recovering at least $CF_3CH$=CHF (1234ze), and operating a refrigeration system comprising the recovered $CF_3CH$=CHF (1234ze).

49. The process of any of claims 17 or 36 further comprising recovering at least $CF_3CH$=CHF (1234ze) and $CF_3CH$=CHF (1234yf) and operating a refrigeration system comprising the recovered 1234ze and 1234yf.

50. The process of claim 36 further comprising recovering and converting at least $CF_3CH_2CHF_2$ (245fa) and $CF_3CF_2CH_3$ (245cb) to additional $CF_3CH{=}CHF$ (1234ze) and $CF_3CH$=CHF (1234yf) and operating a refrigeration system with at least $CF_3CH$=CHF (1234ze).

51. A mixture comprising $CF_3CCl{=}CH_2$ (1233xf), $CF_3CF{=}CH_2$ (1234yf) E/Z-$CF_3CH$=CHF (1234ze), E/Z-$CF_3CH{=}CHCl$ (1233zd), $CF_3CCl{=}CHCl$ (HCFC-1223xd) and $CF_3CH_2CHF_2$ (245fa).

52. The mixture of claim 51 comprising $CF_3CClFCHF_2$ (226ba).

53. A mixture consisting essentially of $CF_3CCl{=}CH_2$ (1233xf), $CF_3CF_2CH_3$ (245cb), $CF_3CF{=}CH_2$ (1234yf) $CF_3CH$=CHF (1234ze) E/Z-$CF_3CH$=CHCl (12332d) and $CF_3CH_2CHF_2$ (245fa).

54. A mixture consisting essentially of $CF_3CCl{=}CH_2$ (1233xf) $CF_3CF{=}CH_2$ (1234yf), E/Z-$CF_3CH$=CHF (1234ze) and E/Z-$CF_3CH{=}CHCl$ (1233zd).

55. A refrigerant comprising $CF_3CH{=}CHF$ (123426) and 1.1.1.2.2-Pentafluoropropane (245cb) both formed from the process of claim 22 and separated from the product mixture.

56. An air conditioner containing $CF_3CH$=CHF (1234ze) and 1.1.1.2.2-Pentafluoropropane (245cb) both formed from the process of claim 22 and separated from the product mixture.

57. The process of any of claims 22 or 23 further comprising recovering the product and providing the recovered product as a blowing agent or propellant component.

58. The process of claim 17 wherein the chlorofluorination catalyst comprises $Cr_2O_3$ with Cobalt.

59. The process of claim 17 wherein the chlorofluorination catalyst comprises mixtures of chromium and other metals selected from the group of elemental metals, metal oxides, metal halides, metal salts and combinations thereof.

60. The process of claim 17 wherein the chlorofluorination catalyst comprises $Cr_2O_3$ with other metals selected from magnesium halides or zinc halides supported on $Cr_2O_3$.

61. The process of claim 17 wherein the chlorofluorination catalyst comprises chromium(III) halides supported on carbon.

62. The process of claim 17 wherein the chlorofluorination catalyst comprises α- $Cr_2O_3$ and cobalt.

* * * * *